US00PP15018P2

(12) United States Plant Patent
Bergman

(10) Patent No.: US PP15,018 P2
(45) Date of Patent: Jul. 13, 2004

(54) CHRYSANTHEMUM PLANT NAMED 'CORAL YOGRACELAND'

(50) Latin Name: *Chrysanthemum×morifolium*
Varietal Denomination: Coral Yograceland

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/676,701

(22) Filed: Oct. 1, 2003

(51) Int. Cl.[7] ..... A01H 5/00

(52) U.S. Cl. ..... Plt./297

(58) Field of Search ..... Plt./297, 286

*Primary Examiner*—Bruce R. Campell
*Assistant Examiner*—June Hwu
(74) *Attorney, Agent, or Firm*—C. A. Whealy

(57) ABSTRACT

A distinct cultivar of Chrysanthemum plant named 'Coral Yograceland', charcaterized by its uniform and outwardly spreading plant habit; strong and freely branching growth habit; dark green-colored foliage; uniform flowering response and habit; early flowering habit; large anemone-type inflorescences; coral pink-colored ray florets; and good postproduction longevity with plants maintaining good substance and color for about three to four weeks in an interior environment.

2 Drawing Sheets

Botanical classification/cultivar designation: *Chrysanthemum×morifolium* cultivar Coral Yograceland.

BACKGROUND OF THE INVENTION

The present Invention relates to a new and distinct cultivar of Chrysanthemum plant, botanically known as *Chrysanthemum×morifolium* and hereinafter referred to by the name 'Coral Yograceland'.

The new Chrysanthemum is a product of a planned breeding program conducted by the Inventor in Fort Myers, Fla. The objective of the program is to create or discover new potted Chrysanthemum cultivars that are suitable for year-round production with uniform plant growth habit, good vigor and strong branching habit, numerous inflorescences, desirable inflorescence form and floret colors, fast and uniform flowering response, and good postproduction longevity.

The new Chrysanthemum is a naturally-occurring whole plant mutation of the Chrysanthemum cultivar Pink Yograceland, disclosed in U.S. Plant Pat. No. 12,950. The new Chrysanthemum was discovered and selected by the Inventor as a single flowering plant from within a population of flowering plants of Pink Yograceland in January, 2001, in a controlled environment in Fort Myers, Fla. The selection of this plant was based on its uniform plant growth habit, good vigor and strong branching habit, numerous inflorescences, desirable inflorescence form and floret colors, fast and uniform flowering response, and good postproduction longevity.

Asexual reproduction of the new Chrysanthemum by vegetative tip cuttings was first conducted in Fort Myers, Fla. in April, 2001. Asexual reproduction by cuttings has shown that the unique features of this new Chrysanthemum are stable and reproduced true to type in successive generations.

SUMMARY OF THE INVENTION

The cultivar Coral Yograceland has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Coral Yograceland'. These characteristics in combination distinguish 'Coral Yograceland' as a new and distinct Chrysanthemum:

1. Uniform and outwardly spreading plant habit.
2. Strong and freely branching growth habit.
3. Dark green-colored foliage.
4. Uniform flowering response and habit.
5. Early flowering, 8-week response time.
6. Large anemone-type inflorescences.
7. Coral pink-colored ray florets.
8. Good postproduction longevity with plants maintaining good substance and color for about three to four weeks in an interior environment.

Plants of the new Chrysanthemum differ primarily from plants of the cultivar Pink Yograceland primarily in ray floret coloration as plants of the cultivar Pink Yograceland have pink-colored ray florets.

Plants of the new Chrysanthemum differ primarily from plants of the cultivar Honey Yograceland, disclosed in a U.S. Plant patent application No. 10/676,787 filed concurrently, primarily in ray floret coloration as plants of the cultivar Honey Yograceland have light orange bronze-colored ray florets.

Plants of the new Chrysanthemum can be compared to plants of the cultivar Apricot Blush, disclosed in U.S. Plant Pat. No. 9,518. In side-by-side comparisons conducted in Fort Myers, Fla., plants of the new Chrysanthemum differed from plants of the cultivar Apricot Blush in the following characteristics:

1. Plants of the new Chrysanthemum were more vigorous than plants of the cultivar Apricot Blush.
2. Plants of the new Chrysanthemum had anemone-type inflorescences whereas plants of the cultivar Apricot Blush had daisy-type inflorescences.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph on the first sheet comprises a side perspective view of typical flowering plants of 'Coral Yograceland'.

The photograph on the second sheet comprises a close-up view of typical inflorescences of 'Coral Yograceland'.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the spring in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 5,000 to 6,000 foot-candles. Four unrooted cuttings were directly stuck in 15-cm containers, exposed to long day/short night conditions, and pinched once about 14 days later. At the time of the pinch, the photoinductive short day/long night treatments were initiated. Plants used for the photographs and description were grown as disbud-types. Measurements and numerical values represent averages of typical flowering plants.

Botanical classification: *Chrysanthemum×morifolium* cultivar Coral Yograceland.

Commercial classification: Anemone-type potted Chrysanthemum.

Parentage: Naturally-occurring whole plant mutation of the *Chrysanthemum×morifolium* cultivar Pink Yograceland, disclosed in U.S. Plant Pat. No. 12,950.

Propagation:

*Type.*—Terminal tip cuttings.

*Time to initiate roots.*—About four days at 21° C.

*Time to produce a rooted cutting.*—About ten days at 21° C.

*Root description.*—White, close to 155D; fibrous.

*Rooting habit.*—Freely branching.

Plant description:

*Appearance.*—Herbaceous anemone-type potted Chrysanthemum that is typically grown as a natural spray or as a disbud-type. Uniform with lateral branches outwardly spreading; uniformly mounded crown. Strong and freely branching growth habit; about three or four lateral branches develop after removal of terminal apex (pinching); dense and full plants.

*Plant height.*—About 25 cm.

*Plant width.*—About 36 cm.

*Lateral branches* (*peduncles*).—Length: About 18.5 cm. Diameter: About 4 mm. Internode length: About 1 cm. Strength: Strong. Texture: Pubescent. Color: Close to 146A.

*Foliage description.*—Arrangement: Alternate; simple. Length: About 7.2 cm. Width: About 4.5 cm. Apex: Mucronate. Base: Truncate. Margin: Palmately lobed, sinuses between lateral lobes parallel to divergent. Texture, upper and lower surfaces: Pubescent. Color: Developing expanded foliage, upper surface: Darker than 147A. Developing expanded foliage, lower surface: Darker than 147B. Fully expanded foliage, upper surface: Close to 147A. Fully expanded foliage, lower surface: Close to 147B. Venation, upper surface: Close to 147A. Venation, lower surface: Close to 147B. Petiole length: About 1.8 cm. Petiole diameter: About 3 mm. Petiole color, upper surface: Close to 146A. Petiole color, lower surface: Close to 146B to 146C.

Inflorescence description:

*Appearance.*—Anemone-type inflorescence form with elongated oblong-shaped ray florets. Inflorescences borne on terminals above foliage. Disk and ray florets develop acropetally on a capitulum. Inflorescences not fragrant. Plants can be grown as natural spray or as disbud-types.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to two weeks of long day/short night conditions followed by photoinductive short day/long night conditions flower about eight weeks later.

*Postproduction longevity.*—Inflorescences maintain good color and substance for about three to four weeks in an interior environment.

*Quantity of inflorescences.*—Grown as a disbud-type, only one inflorescence develops per lateral branch.

*Inflorescence bud.*—Height: About 5 mm. Diameter: About 8 mm. Shape: Oblate. Color: Close to 146A.

*Inflorescence diameter.*—Large, about 13.75 cm.

*Inflorescence depth* (*height*).—About 2.5 cm.

*Diameter of disc.*—About 4.5 cm.

*Receptacle diameter.*—About 8 mm.

*Ray florets.*—Shape: Elongated oblong. Orientation: Initially upright, then perpendicular to the peduncle and eventually reflexing. Aspect: Flat to arching. Length: About 6.5 cm. Corolla tube length: About 2 mm. Width: About 1.5 cm. Apex: Emarginate. Base: Fused into a corolla tube. Margin: Entire. Texture: Smooth, glabrous, satiny. Number of ray florets per inflorescence: About 24 arranged in one to two whorls. Color: When opening and fully opened, upper surface: Close to 5C faintly overlain with 59A. When opening and fully opened, lower surface: Close to 5C faintly underlain with close to 59A.

*Disc florets.*—Arrangement: Massed at center of receptacle. Shape: Tubular, enlarged. Apex: Five-pointed. Length: About 1.8 cm. Diameter, apex: About 6 mm. Diameter, base: About 2 mm. Number of disc florets per inflorescence: About 152. Color: Immature: Close to 151A. Mature: Apex: Close to 9A. Midsection: Close to 9C. Base: Close to 155D. Throat: Towards the apex, close to 9A, towards the base, close to 9C.

*Phyllaries.*—Quantity per inflorescence: About 22. Length: About 8 mm. Width: About 3 mm. Shape: Deltoid. Apex: Acute. Base: Truncate. Margin: Entire. Texture, upper surface: Waxy, smooth. Texture, lower surface: Pubescent. Color, upper surface: Close to 146B to 146C. Color, lower surface: Close to 146A.

*Reproductive organs.*—Androecium: Present on disc florets only. Anther color: Close to 12A. Pollen amount: None observed. Gynoecium: Present on both ray and disc florets. Style color: Close to 144B to 144C. Stigma color: Close to 9A.

*Seed/fruit.*—Seed and fruit production has not been observed.

Disease/pest resistance: Resistance to pathogens and pests common to Chrysanthemums has not been observed on plants grown under commercial greenhouse conditions.

It is claimed:

1. A new and distinct cultivar of Chrysanthemum plant named 'Coral Yograceland', as illustrated and described.

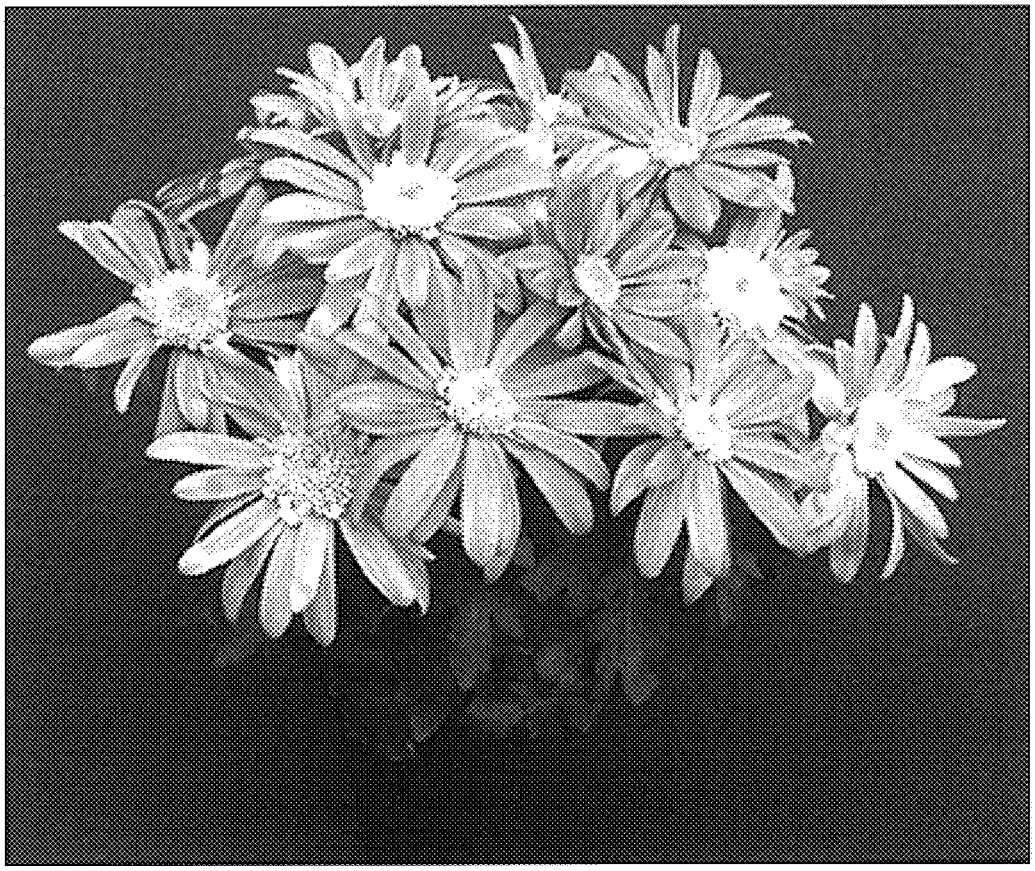

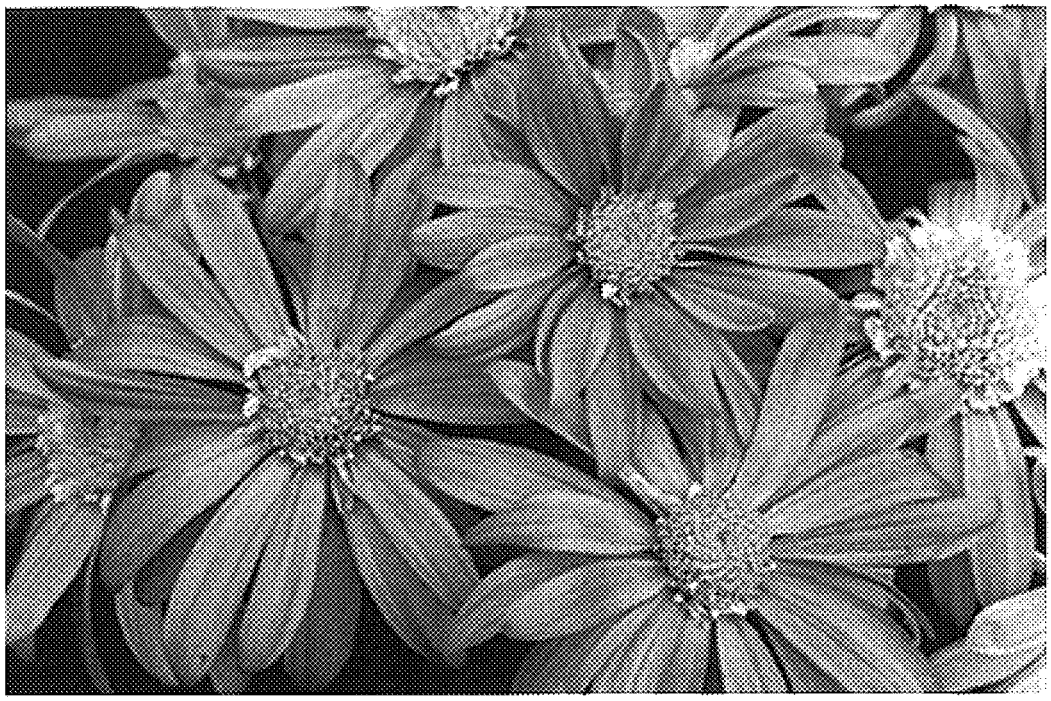

* * * * *